(12) United States Patent
Polymeropoulos et al.

(10) Patent No.: US 10,987,346 B2
(45) Date of Patent: *Apr. 27, 2021

(54) ILOPERIDONE FOR THE TREATMENT OF SCHIZOPHRENIA

(71) Applicant: Vanda Pharmaceuticals, Inc., Washington, DC (US)

(72) Inventors: Mihael H. Polymeropoulos, Potomac, MD (US); Curt D. Wolfgang, Germantown, MD (US)

(73) Assignee: Vanda Pharmaceuticals Inc., Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/562,548

(22) Filed: Sep. 6, 2019

(65) Prior Publication Data

US 2019/0388412 A1  Dec. 26, 2019

Related U.S. Application Data

(63) Continuation of application No. 15/549,820, filed as application No. PCT/US2016/018316 on Feb. 17, 2016, now Pat. No. 10,441,580.

(60) Provisional application No. 62/117,173, filed on Feb. 17, 2015, provisional application No. 62/172,436, filed on Jun. 8, 2015.

(51) Int. Cl.
  *A61K 31/454*  (2006.01)

(52) U.S. Cl.
  CPC .................... *A61K 31/454* (2013.01)

(58) Field of Classification Search
  CPC .................................. A61K 31/454
  USPC ......................................... 514/326
  See application file for complete search history.

(56) References Cited

U.S. PATENT DOCUMENTS

| 9,439,906 | B2 | 9/2016 | Vermeulen et al. |
| 2010/0063093 | A1 | 3/2010 | Wolfgang et al. |
| 2014/0350029 | A1 | 11/2014 | Loebel |

FOREIGN PATENT DOCUMENTS

| WO | 2006039663 A2 | 4/2006 |
| WO | 2009036056 A1 | 3/2009 |
| WO | 2010132866 A1 | 11/2010 |
| WO | 2014031792 A2 | 2/2014 |

OTHER PUBLICATIONS

Rado et al., Neuropsychiatric Dis. and Treatment (2014) vol. 10, pp. 409-415.*
International Search Report and Written Opinion for International Application No. PCT/US2016/018316 dated Apr. 21, 2016, 15 pages.
Caccia et al., "New atypical antipsychotics for schizophrenia: iloperidone", Drug Design, Development and Therapy, 2010:4 33-48.
Crabtree al., "Iloperidone for the Management of Adults with Schizophrenia" Clinical Therapeutics, vol. 33, No. 3, 2011, 8 pages.
Hale et al., "Iloperidone—A Second-Generation Antipsychotic for the Treatment of Acute Schizophrenia", J Pharm. Technol., vol. 26, Jul./Aug. 2010, 5 pages.
Scott, "Iloperidone in Schizophrenia", CNS Drugs, 2009, 23(10) pp. 867-880.
Weiden et al. "Safety Profile of Iloperidone: A Pooled Analysis of 6-Week Acute-Phase Pivotal Trials", Journal of Clinical Psychopharmacology, vol. 28, No. 2, Supplement 1, Apr. 2008, 4 pages.
Vanda Pharm. Inc.; "FANAPT (iloperidone) Tablets Highlights of Prescribing Information"; May 2009; pp. 1-23.
Vanda Pharm. Inc.; "Highlights of Prescribing Information"; Ref. ID: 3492157; Apr. 2014; pp. 1-20.

* cited by examiner

*Primary Examiner* — Taofiq A Solola
(74) *Attorney, Agent, or Firm* — Hoffman Warnick LLC

(57) ABSTRACT

Aspects of the invention relate generally to the treatment of schizophrenia in an individual and, more specifically, to the treatment of an individual with iloperidone, an iloperidone metabolite, or a pharmaceutically-acceptable salt thereof. In one embodiment, the invention provides a method of preventing schizophrenic relapse in an individual diagnosed with schizophrenia, the method comprising: administering to the individual iloperidone, an iloperidone metabolite, or a pharmaceutically-acceptable salt thereof at a daily dose between about 12 mg and about 16 mg following a period in which the individual's schizophrenia was stabilized.

13 Claims, 4 Drawing Sheets

ILOPERIDONE FOR THE TREATMENT OF SCHIZOPHRENIA

CROSS REFERENCE TO RELATED APPLICATIONS

This application is a continuation of U.S. application Ser. No. 15/549,820, filed Aug. 9, 2017, which is a US national phase of International Application No. PCT/US2016/018316, filed Feb. 17, 2016, which claims the benefit of U.S. Provisional Application No. 62/117,173, filed Feb. 17, 2015, and U.S. Provisional Application No. 62/172,436, filed Jun. 8, 2015, all of which are incorporated herein as though fully set forth.

BACKGROUND

This invention relates generally to a method of treating schizophrenia, and more particularly to a method of treating schizophrenia with iloperidone, an iloperidone metabolite, or a pharmaceutically acceptable salt thereof.

Schizophrenia is a lifelong disorder, with most patients following a relapse course for life. Long-term efficacy, tolerability, and adherence to medication are important clinical issues in the management of schizophrenia.

Iloperidone, a mixed $D_2$, $5\text{-}HT_{2A}$, and $\alpha_1$-adrenergic antagonist, is an atypical antipsychotic agent that was approved by the US FDA for the treatment of schizophrenia in adults in 2009 based on short-term acute efficacy studies. The acute and long-term efficacy and safety of iloperidone has been demonstrated in four short-term (4- and 6-week) and three long-term (52-week) studies. Subsequently, a study was conducted to evaluate the safety and effectiveness of long-term flexible dosing of iloperidone (8-24 mg/day) compared with placebo for maintenance treatment of schizophrenia, and prevention of relapse or impending relapse of schizophrenia.

BRIEF DESCRIPTION OF THE INVENTION

A first aspect of the invention provides a method of treating schizophrenia in an individual, the method comprising: administering to the individual a first daily dose of iloperidone, an iloperidone metabolite, or a pharmaceutically-acceptable salt thereof during an acute treatment phase, followed by administering to the individual a second daily dose of iloperidone, an iloperidone metabolite, or a pharmaceutically-acceptable salt thereof during a maintenance treatment phase. In this aspect of the invention, the acute treatment phase follows an initial titration of iloperidone, and the second daily dose is smaller than the first daily dose.

A second aspect of the invention provides a method of preventing schizophrenic relapse in an individual diagnosed with schizophrenia, the method comprising: administering to the individual iloperidone, an iloperidone metabolite, or a pharmaceutically-acceptable salt thereof at a daily dose between about 12 mg and about 16 mg following a period in which the individual's schizophrenia was stabilized.

A third aspect of the invention provides a method to maintain the effect of iloperidone for schizophrenia after response in an acute phase has been obtained, the method comprising: administering to the individual a quantity of iloperidone, an iloperidone metabolite, or a pharmaceutically-acceptable salt thereof at a daily dose between about 12 mg and about 16 mg.

A fourth aspect of the invention provides a method of maintaining control of symptoms in a patient suffering from schizophrenia, after the patient has been stabilized, e.g., by internal administration of 12-24 mg/day of iloperidone for a period of up to 6 weeks, the method including continuing to administer iloperidone at a daily dose of 12-24 mg/day, or 12-16 mg/day following the initial stabilization period.

A fifth aspect of the invention provides a method of treating schizophrenia or at least one symptom of schizophrenia with administration of iloperidone, an iloperidone metabolite, or a pharmaceutically-acceptable salt thereof, in a decreasing amount, e.g., starting treatment in an amount of 12-24 mg/day, and evaluating efficacy in the individual. Following determination of efficacy, iloperidone may be administered in an amount of 12-16 mg/day as a maintenance therapy. In the event that no efficacy is observed, another antipsychotic may be administered.

These and other aspects, advantages, and salient features of the invention will become apparent from the following detailed description.

DETAILED DESCRIPTION OF THE INVENTION

Figure 1:
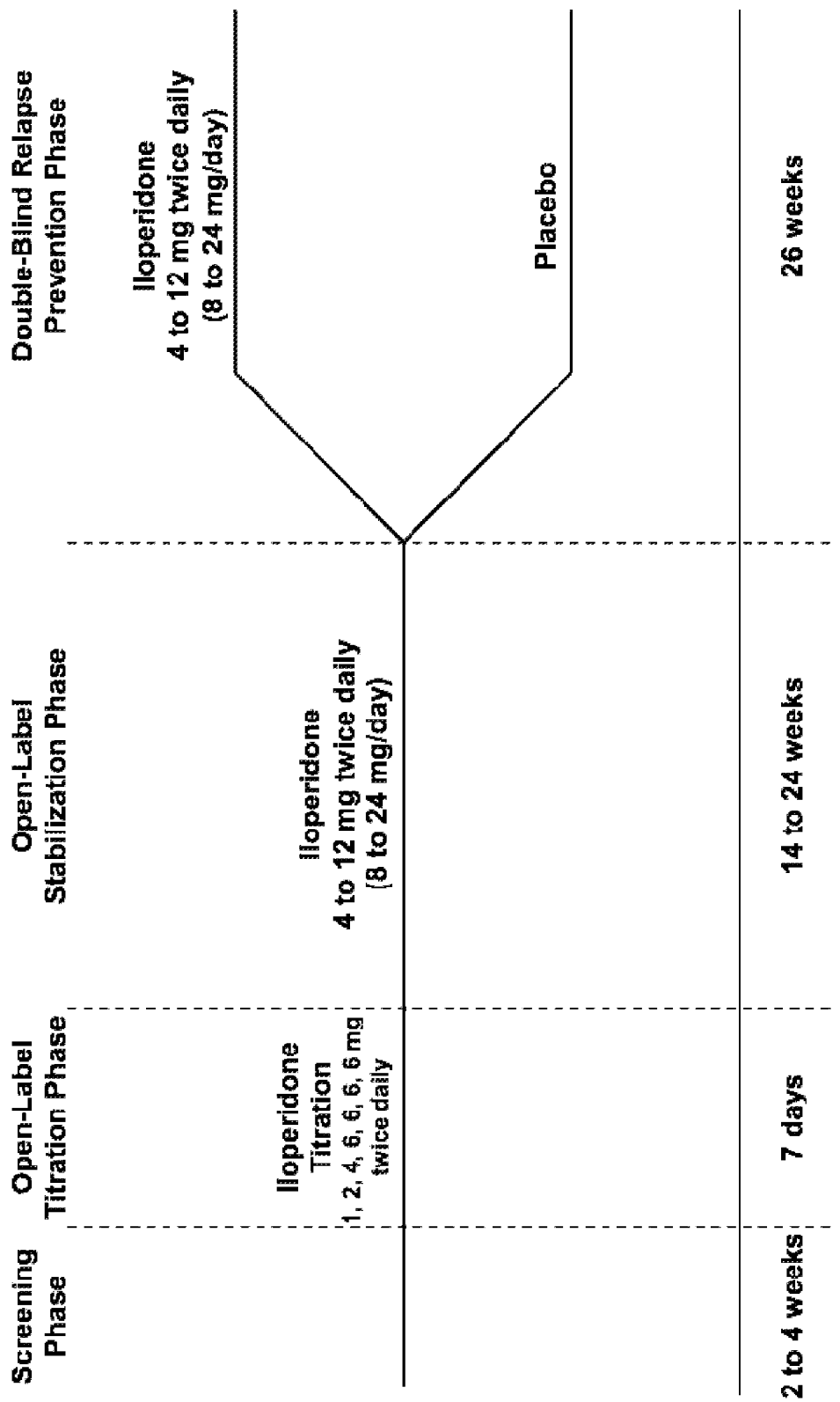
FIG. 1 illustrates the screening phase, open-label titration phase, open-label stabilization phase, double-blind randomized withdrawal phase of a study described herein.

For patients with stable symptoms of schizophrenia, maintenance treatment with iloperidone can prevent or delay relapse of symptoms.

Although passages herein refer to administration of "iloperidone," according to embodiments of the invention, it is understood that a patient in need of treatment may be administered iloperidone, an iloperidone metabolite, or pharmaceutically-acceptable salts thereof. Iloperidone metabolites include the metabolite P88, including its enantiomer forms, S-P88 and R-P88. The S-P88 and/or R-P88 metabolites of iloperidone are described in International Patent Application Publication Nos. WO2003/020707 and WO2013/138602, as well as U.S. Pat. Nos. 7,977,356 and 8,314,129, each of which is incorporated herein by reference as though fully set forth.

Iloperidone, iloperidone metabolites, or pharmaceutically-acceptable salts thereof may be administered in any number of manners, as will be recognized by one skilled in the art. Oral administration may be typical, but other routes include, for example, parenteral, nasal, buccal, transdermal, sublingual, intramuscular, intravenous, rectal, vaginal, etc.

According to some embodiments of the invention, iloperidone, an iloperidone metabolite, or a pharmaceutically-acceptable salt thereof may be administered in depot form. Such depot forms are described, for example, in U.S. Pat. Nos. 7,767,230; 8,815,293; 8,293,765; 8,227,488; and 8,614,232, each of which is incorporated herein by reference as though fully set forth. One skilled in the art will understand that, when administered in depot form, the phrase "daily dose" used herein refers to an expected or intended dose to which the individual is effectively exposed during the course of a day.

As described herein, daily doses of iloperidone, an iloperidone metabolite, or a pharmaceutically-acceptable salt administered during an acute treatment setting (referred to herein as a "first daily dose") may be different from daily doses administered during a long-term maintenance setting (referred to herein as a "second daily dose"). That is, a first daily dose is intended to refer to a dose administered during the acute treatment setting following the initial titration of iloperidone, whereas a second daily dose is intended to refer to a dose administered during the long-term maintenance setting. For schizophrenia patients who have become stabilized, the second dose, i.e. maintenance therapy, may be a recommended dose of 6-8 mg/day twice daily (12-16 mg/day).

Therefore, instructions for carrying out embodiments of this invention may include all or portions of the following statements or variants thereof:

Patients must be titrated to an effective dose of iloperidone. Thus, control of symptoms may be delayed during the first 1 to 2 weeks of treatment compared to some other antipsychotic drugs that do not require a similar titration. Prescribers should be mindful of this delay when selecting an antipsychotic drug for the treatment of schizophrenia;

and/or

Iloperidone must be titrated slowly from a low starting dose to avoid orthostatic hypotension due to its alpha-adrenergic blocking properties. The recommended starting dose for iloperidone tablets is 1 mg twice daily. Dose increases to reach the target range of 6 to 12 mg twice daily (12 to 24 mg/day) may be made with daily dosage adjustments not to exceed 2 mg twice daily (4 mg/day). The maximum recommended dose is 12 mg twice daily (24 mg/day). Iloperidone doses above 24 mg/day have not been systematically evaluated in the clinical trials. Efficacy was demonstrated with iloperidone in a dose range of 6 to 12 mg twice daily. Prescribers should be mindful of the fact that patients need to be titrated to an effective dose of iloperidone. Thus, control of symptoms may be delayed during the first 1 to 2 weeks of treatment compared to some other antipsychotic drugs that do not require similar titration. Prescribers should also be aware that some adverse effects associated with iloperidone use are dose related and/or For patients with stable symptoms of schizophrenia, Maintenance Treatment with iloperidone can prevent or delay relapse. The recommended dose range is 6 to 8 mg twice daily (12 to 16 mg/day).

EXAMPLE 1

1. Methods

Overview

Study subjects were adults with schizophrenia who were first treated with open-label iloperidone 12 mg/day given as 6 mg BID and then stabilized for a further 14-24 weeks with a flexible-dose iloperidone regimen as per investigator judgment ranging between 8-24 mg/day daily dose (given BID). Subjects who remained clinically stable for at least 12 weeks entered the relapse prevention phase and were randomized 1:1 to either continue on the same flexible dose regimen of iloperidone or to withdraw from iloperidone to matched placebo in a double-blinded fashion. Subjects were followed for up to 26 weeks and were withdrawn upon showing signs of relapse or impending relapse. A pre-defined unblinded interim analysis (IA) was conducted utilizing a group sequential testing procedure with an O'Brien-Fleming stopping boundary after 68 relapse or impending relapse events were observed. The primary outcome was time-to-relapse or impending relapse with event criteria defined in the protocol prior to first subject enrollment.

Study Design

A randomized, double-blind, placebo-controlled, parallel-group study (ClinicalTrials.gov identifier NCT01291511) was performed at 27 centers in the United States, 15 in India and 24 in Ukraine. Key inclusion and exclusion criteria for the patient population are listed in Table 1 below.

TABLE 1

Key Inclusion/Exclusion Criteria

| Inclusion Criteria | Exclusion Criteria |
| --- | --- |
| Males or females, 18 to 65 years of age, inclusive | DSM-IV diagnosis of schizophreniform disorder or schizoaffective disorder |
| DSM-IV diagnosis of schizophrenia for at least 1 year | Any other Axis I or Axis II disorder |
| BMI > 17 and < 40 kg/m$^2$ | Treatment naive, first episode schizophrenia |
| PANSS Total score ≤100 and CGI-S ≤ 5 at screening | Patients whose psychotic symptoms failed to improve following sufficient exposure to 2 antipsychotic treatments within 2 years of screening |
| Had a history of ≥ 2 prior episodes of relapse or impending relapse within 2 years of screening | Patients hospitalized due to suicidal ideation within 6 months of screening, or suicidal behavior within 2 years of screening |
| Patients were not inpatients for at least 1 week prior to screening | Significant cardiovascular illness (e.g., myocardial infarction, cardiac arrhythmia) or baseline QTcF ≥ 450 msec |

The study consisted of five phases, the first four of which are shown in FIG. 1: screening phase, open-label titration phase, open-label stabilization phase, double-blind randomized withdrawal phase, and open-label extension phase (not shown).

In the Open-Label Titration Phase, patients received iloperidone 1, 2, 4, 6, 6, 6, 6 mg twice daily on Days 1 through 7, respectively. All previous antipsychotic treatments were discontinued prior to, or within 4 days, after the first day of iloperidone treatment. If the Investigator felt that it was necessary to titrate down the previous antipsychotic medication, the dose reduction was to be done within the first 4 days initiating iloperidone treatment (i.e., previous medication fully discontinued by Day 4).

In the Open-Label Stabilization Phase, patients received flexible doses of iloperidone 4 to 12 mg twice daily (8 to 24 mg/day). Patients needed to be clinically stable for a minimum of 12 weeks prior to randomization.

In the Double-Blind Randomized Withdrawal Phase, patients were randomized to receive iloperidone or placebo. Patients randomized to iloperidone initially took the dose level being received during the last 4 weeks of the Stabilization Phase and then treated with flexible doses of iloperidone 4 to 12 mg twice daily (8 to 24 mg/day).

The Open-Label Extension Phase is not reported here.

Patients needed to be clinically stable throughout the last 12 weeks of the Stabilization Phase to be eligible for randomization. "Clinically stable" adult outpatients were defined as: meeting DSM-IV criteria for schizophrenia, and remaining stable following 12 weeks of open-label treatment with flexible doses of iloperidone, being on an established dose of iloperidone that remained unchanged due to efficacy during the 4 weeks prior to randomization; PANSS total score ≤70 and CGI-S score ≤4; Score of ≤4 on each of the following individual PANSS items: P1 (delusion), P2 (conceptual disorganization), P3 (hallucinatory behavior), P6 (suspiciousness/persecution), P7 (hostility), or G8 (uncooperativeness); and no hospitalization or increase in level of care to treat exacerbations.

This study was conducted in accordance to the ethical principles of the Declaration of Helsinki, Good Clinical Practices, and applicable regulatory guidelines.

The primary efficacy endpoint was time to relapse or impending relapse. Relapse or impending relapse during the double-blind relapse prevention phase was defined as any of the following: hospitalization (voluntary or involuntary) due to worsening of schizophrenia; an increase (worsening) of the PANSS total score of ≥30% from randomization, confirmed at a second visit conducted with 1 to 7 days later; patient had clinically significant suicidal, homicidal, or aggressive behavior; CGI-I score of ≥6 (much worse) or 7 (very much worse) after randomization; or an increase in iloperidone dose or in need of additional antipsychotic treatment. Dose reductions for tolerability were not considered as a relapse or impending relapse.

The primary efficacy endpoint was based on a pre-specified interim analysis to be performed by an independent Data Monitoring Committee (iDMC) after 68 events (relapse or impending relapse) occurred. If significant efficacy was observed, the study would be stopped. Events occurring after the interim analysis were included in the Full Analysis Set (FAS) and analyzed as confirmatory evidence. Secondary efficacy variables included the change from randomization to end point for PANSS (total, positive, negative and general psychopathology) scores, 18-item BPRS, Clinical Global Impression of Improvement and Severity (CGI-I and CGI-S) and the Sheehan Disability Scale (SDS).

Safety assessments included collection of adverse events (AEs), clinical laboratory evaluations, 12-lead electrocardiograms (ECGs), body weight, vital signs, Columbia Suicide Severity Rating Scale (C-SSRS), and movement disorder rating scales (Barnes Akathisia Scale [BAS], Abnormal Involuntary Movement Scale [AIMS], and Simpson Angus Scale [SAS]).

Primary efficacy analysis of time to relapse of impending relapse was the log rank test. A pre-defined unblinded interim analysis was conducted utilizing a group sequential testing procedure with an O'Brien-Fleming stopping boundary after 68 relapse or impending relapse events were observed. The log-rank tests to compare the time to relapse (or impending relapse) between iloperidone and placebo were examined at the 0.001 alpha level for the interim analysis and at the 0.048 alpha level time for the final analysis. Results from the interim analysis were considered the primary results, and results from the FAS population are considered supportive.

Plots of the Kaplan-Meier (KM) product limit estimates were used to summarize survival distributions; Cox regression model provided an estimated hazard ratio and 95% confidence interval (CI); and changes in secondary endpoints with continuous endpoints (PANSS, BPRS, SDS, CGI-I, CGI-S) were compared using an analysis of covariance (ANCOVA) with treatment and site as main effects and the score at randomization as a covariate.

Efficacy analysis was based on the FAS population, which contained all randomized patients who received at least 1 dose of study medication and from whom at least 1 efficacy measurement was obtained while on study medication.

The safety population was defined for each study phase (Titration and Stabilization or Double-Blind Relapse Prevention). For each phase, the safety population included all patients who received at least 1 dose of study medication during the corresponding phase. Descriptive statistics by study phase for each of the safety assessments were calculated.

2. Results

Overview

Of the 587 subjects entering the stabilization phase in the Interim Analysis (IA), 195 (33%) met the criteria for the double-blind relapse prevention phase, with 99 subjects randomized to continue with iloperidone and 96 to switch to placebo. Of the 635 subjects entering the Stabilization phase in the final analysis set (FAS), 303 (48%) met the criteria for the DBRP, with 153 subjects randomized to continue with iloperidone and 150 to switch to placebo. Modal daily dose for iloperidone in all phases of the study was 12 mg/day. The study was stopped early after 68 events were observed and confirmed the hypothesis that iloperidone was more effective than placebo in relapse preventions (log rank test: p<0.0001), with estimated relapse rates at the end of the double-blind relapse prevention phase of 63.4% (KM est.) for the placebo group compared to 20.4% (KM est.) for those staying on iloperidone. The mean time to relapse based on KM estimates was 71 days for placebo and 139 days for iloperidone subjects, with a Cox regression hazard ratio estimate of 4.7 (95% CI: 2.7-8.3) favoring iloperidone (p<0.0001). The hazard ratio for the final analysis set (FAS) similarly favored iloperidone (5.2, 95% CI: 3.2, 8.4). The safety profile observed in previous short term studies was also reaffirmed in this maintenance treatment setting.

The most common adverse events (AEs) suspected to be related to iloperidone in the stabilization phase were dizziness, somnolence and dry mouth. There were no iloperidone treatment-related adverse events with a frequency >2% and higher than placebo in the double-blind relapse prevention phase. There were no notable differences in serious adverse events or incidence of clinically notable abnormalities in hematology or chemistry parameters except that 4.5% and 2.6% of patients had elevations in blood urea nitrogen and LDL, respectively, on iloperidone versus none on placebo.

The iDMC stopped the study due to statistically significant efficacy observed (p<0.0001). Efficacy data shown herein are derived from the Interim Analysis Population and Safety data are derived from the Full Analysis Population. Tables 2 and 3 below detail Patient Disposition (Enrolled/Randomized Patients) for the Interim Analysis Population used for Efficacy Assessments, and Demographic Characteristics (Enrolled/Randomized Patients) for the Interim Analysis Population used for Efficacy Assessments, respectively.

TABLE 2

Patient Disposition (Enrolled/Randomized Patients) - Interim Analysis Population used for Efficacy Assessments

| | Titration/ Stabilization Phase | Relapse Prevention Phase | | |
|---|---|---|---|---|
| | Total n (%) | Iloperidone n (%) | Placebo n (%) | Total n (%) |
| Number screened | 991 | | | |
| Number Enrolled in Phase or Randomized[1] | 587 (58) | 99 (17) | 96 (16) | 195 (33) |
| Number Completed the Phase[2] | 201 (34) | 62 (63) | 66 (69) | 128 (66) |
| Number Discontinued During the Phase[2] | 247 (42) | 23 (23) | 12 (13) | 35 (18) |
| Primary Reason for Discontinuation[3] | | | | |
| Adverse Event(s) | 80 (32) | 3 (13) | 0 | 3 (9) |
| Abnormal Laboratory Value(s) | 19 (8) | 3 (13) | 2 (17) | 5 (14) |
| Abnormal Test Procedure Result(s) | 5 (2) | 1 (4) | 0 | 1 (3) |
| Unsatisfactory Therapeutic Effect | 20 (8) | 0 | 0 | 0 |
| Withdrew Consent | 86 (35) | 8 (35) | 7 (58) | 15 (43) |
| Lost to Follow-up | 18 (7) | 6 (26) | 3 (25) | 9 (26) |
| Administrative Problems | 8 (3) | 1 (4) | 0 | 1 (3) |
| Death | 1 (<1) | 1 (4) | 0 | 1 (3) |
| Protocol Deviation | 10 (4) | 0 | 0 | 0 |

[1]Percentage based on the total number of patients from previous phase: patients screened (Titration and Stabilization phases) or patients enrolled (Double-Blind Relapse Prevention phase).
[2]Percentage based on the total number of patients enrolled (Titration and Stabilization phases) or randomized (Double-Blind Relapse Prevention phase).
[3]Percentage based on the total number of patients discontinued during the phase. The study was discontinued following the interim analysis per the iDMC recommendation. The reason for discontinuation was assigned to "Administrative problems."

TABLE 3

Demographic Characteristics (Enrolled/Randomized Patients) - Interim Analysis Population used for Efficacy Assessments

| | Titration/ Stabilization Phase | Relapse Prevention Phase | | |
|---|---|---|---|---|
| | Total (N = 587) | Iloperidone (N = 99) | Placebo (N = 96) | Total (N = 195) |
| Age (years)[1] | 39.4 (11.3) | 38.3 (11.2) | 39.9 (11.0) | 39.1 (11.1) |
| Sex N (%) | | | | |
| Male | 369 (63) | 62 (63) | 52 (54) | 114 (59) |
| BMI (kg/m²)[1] | 26.6 (5.6) | 27.2 (5.3) | 26.9 (5.4) | 27.0 (5.3) |
| Race N (%) | | | | |
| Caucasian | 268 (46) | 66 (67) | 67 (70) | 133 (68) |
| Black | 172 (29) | 22 (22) | 22 (23) | 44 (23) |
| Asian | 117 (20) | 5 (5) | 6 (6) | 11 (6) |
| Pacific Islander | 2 (<1) | 1 (1) | 0 | 1 (<1) |
| Other | 28 (5) | 5 (5) | 1 (1) | 6 (3) |
| PANSS Total[1] at Baseline[2] | 76.9 (11.5) | 57.8 (9.5) | 57.1 (9.2) | 57.5 (9.3) |
| N | 582 | 97 | 96 | 193 |

[1]Mean (standard deviation)
[2]Baseline at the beginning of the respective phase.

Efficacy Assessments

Patients randomized into the Relapse Prevention Phase in the IA (N=195) experienced a mean improvement of −19.5±10.1 points on the PANSS total score during the Titration and Stabilization Phase.

Figure 2:
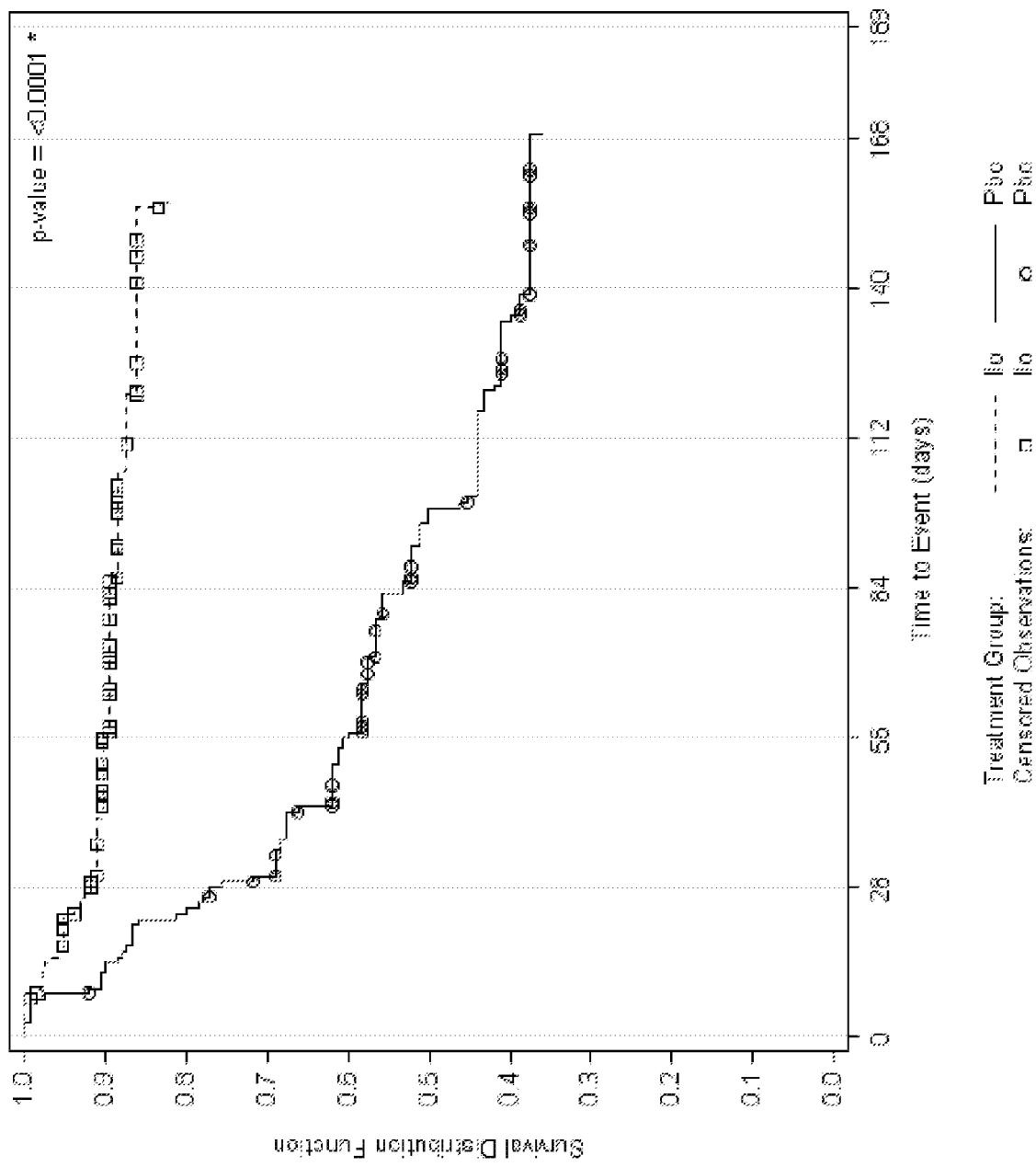
FIG. 2 is a Kaplan-Meier plot of time to relapse or impending relapse for the interim analysis population of the study.

As shown in FIG. 2, in which "Ilo"=iloperidone and "Pbo"=placebo, patients in the iloperidone treatment group experienced a statistically significant longer time to relapse than did patients on placebo. Seventy four percent of patients were treated with doses up to 16 mg per day, and the remaining received doses up to 24 mg per day. Treatment-emergent adverse events were consistent with the adverse events reported in the previously pooled data from short-term studies. Also consistent with prior analyses, QTcF prolongation in this longer-term trial was dose-dependent with higher exposures of FANAPT being associated with more QT prolongation.

Further, as shown in Table 4 below, A longer time to relapse or impending relapse was observed in the iloperidone-treated patients compared to placebo-treated patients.

TABLE 4

Time to Event Analysis

| | Interim Analysis Population | | Final (FAS)* | |
|---|---|---|---|---|
| | Iloperidone (N = 97) | Placebo (N = 96) | Iloperidone (N = 151) | Placebo (N = 150) |
| Relapse Rate (95% CI) | 20.4 (12.9, 31.4) | 63.4 (52.7, 74.1) | 17.9 (11.7, 26.7) | 64.0 (55.0, 72.9) |
| P-value (log-rank test) | <.0001 | | <.0001 | |
| Average Time to Relapse | 139 days | 71 days | 140 days | 95 days |
| Hazard Ratio (95% CI) | 4.7 (2.7, 8.3) | | 5.2 (3.2, 8.4) | |

*FAS = Full Analysis Set

The adjusted mean change from randomization baseline at endpoint in the PANSS total score for the Relapse Prevention Phase was 2.3 points for iloperidone-treated patients versus 16.0 points for placebo-treated patients (p<0.0001, LOCF).

The adjusted mean CGI-I score for the Relapse Prevention Phase was significantly lower in iloperidone-treated patients (3.3) compared with placebo-treated patients (4.2) (p<0.0001, LOCF). The majority of iloperidone-treated patients showed improvement (scores ≤4) while the majority of placebo-treated patients showed worsening (scores >4).

Figure 3:
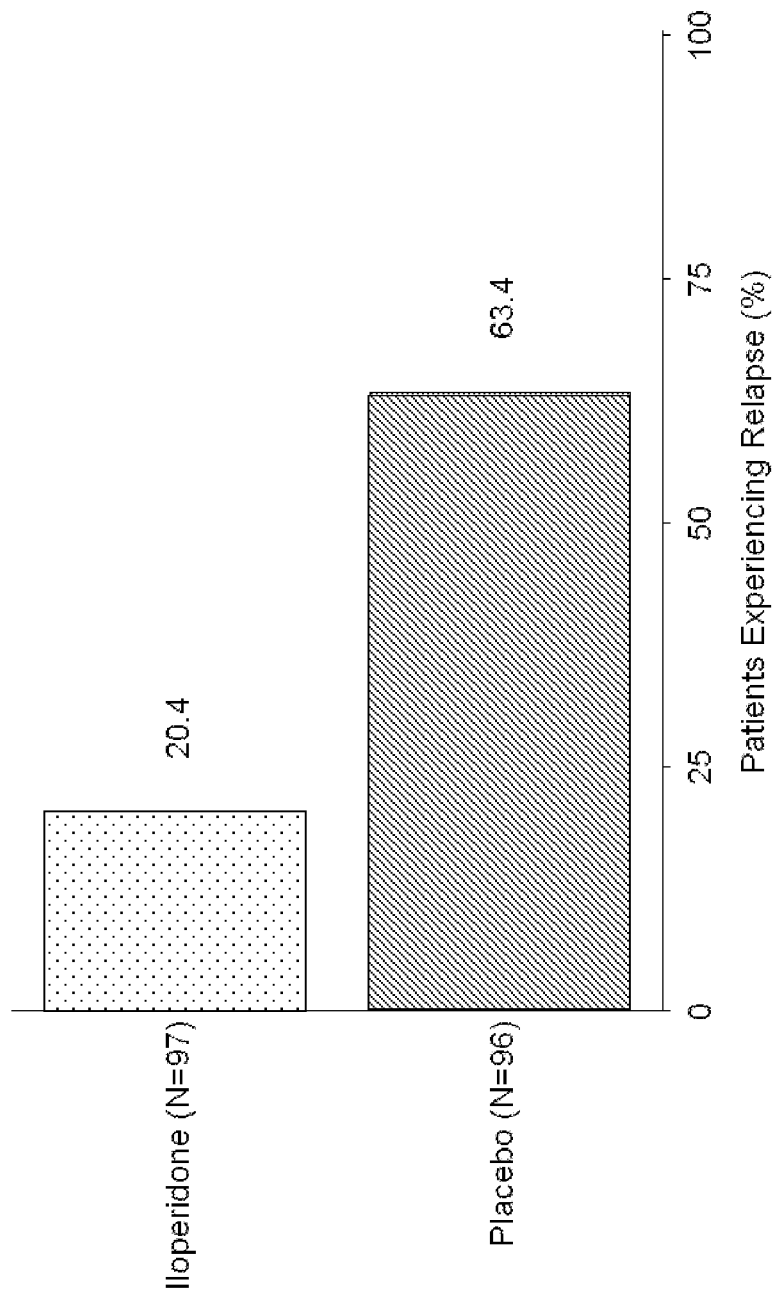
FIG. 3 is a bar chart showing percentage of patients receiving iloperidone and placebo experiencing relapse in the study.
Figure 4:
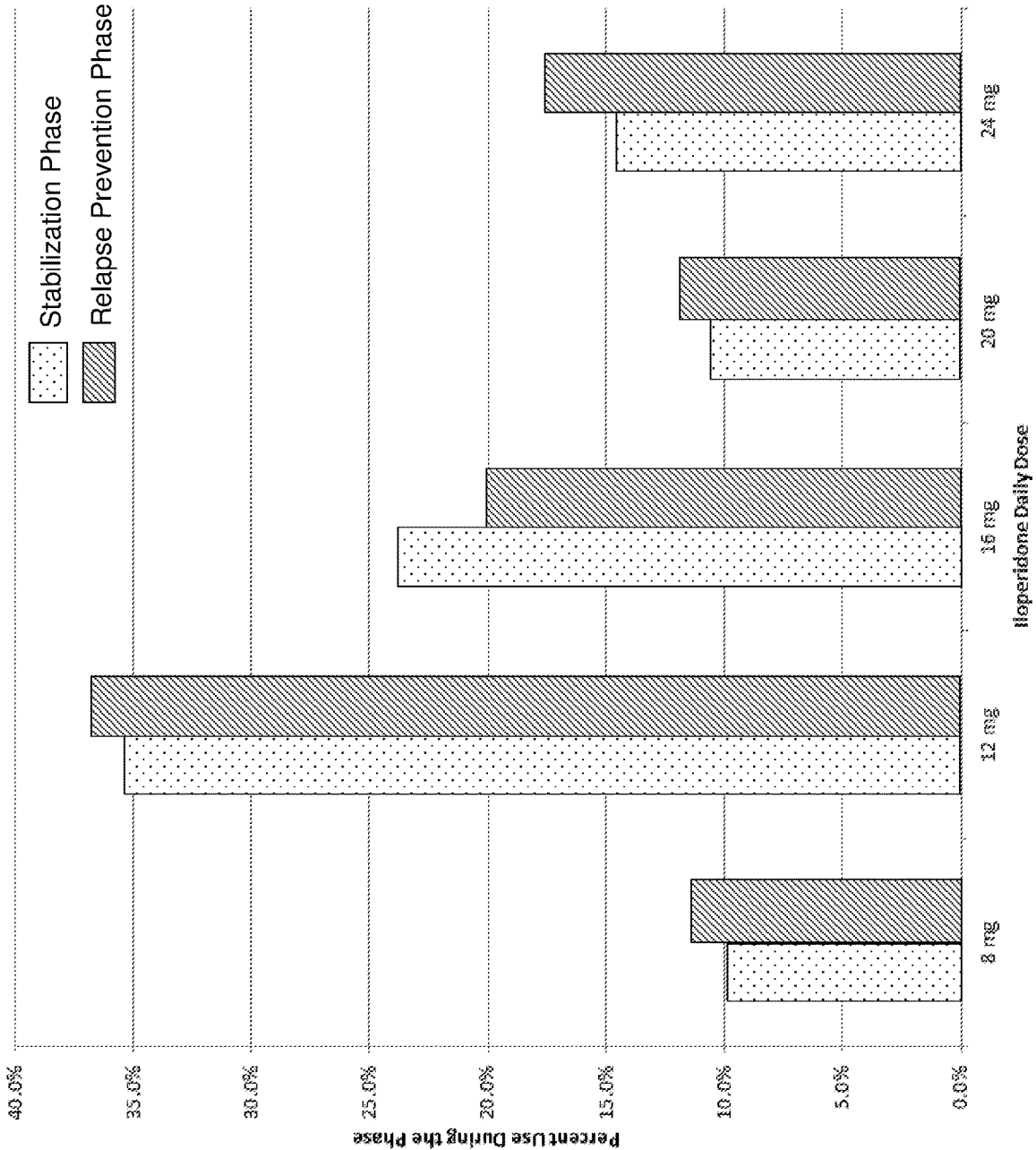
FIG. 4 is a bar chart showing average iloperidone daily dose during the stabilization phase and relapse prevention phase of the study.

As shown in FIG. 3, the average total daily dose for iloperidone during the Titration and Stabilization and Relapse Prevention phases was 13.6±4.5 mg and 15.0±4.9 mg. The modal total daily dose for iloperidone during the Titration and Stabilization and Relapse Prevention phases was 12 mg for each phase.

Table 5, shown below, illustrates time in days to relapse or impending relapse per iloperidone dose (8, 12, 16, 20, and 24 mg/day) for the full analysis population.

TABLE 5

Time to relapse or impending relapse per iloperidone dose - full analysis population

| Dose (Daily) of iloperidone (mg/day) | Number of patients (n) | Avg Time to Relapse or Impending Relapse (Days) |
|---|---|---|
| 8 mg/d | 18 | <30 days |
| 12 mg/d | 58 | >120 days |
| 16 mg/d | 36 | >90 to <120 days |
| 20 mg/d | 14 | >120 days |
| 24 mg/d | 25 | >90 to <120 days |

The most frequently used concomitant medications (≥4%) during the Titration and stabilization phase were: lorazepam (10.8%), zolpidem tartrate (5.9%), and trihexyphenidyl (5.7%), ibuprofen (4.5%). The most frequently used concomitant medications (≥4%) during the Relapse Prevention Phase were: lorazepam (6.0%) and zolpidem tartrate (4.0%). Use of anticholinergics was low in the study. Only 1 patient (0.2%) who participated in the study was treated with ipratropium bromide in the titration and stabilization phase as well as during the relapse prevention phase.

In the Titration and Stabilization Phase, 69% patients treated with iloperidone experienced a Treatment-Emergent Adverse Events (TEAE), and 4% patients treated with iloperidone experienced a SAE. The most common SAE was schizophrenia (1.4%). No other SAEs occurred in >1 patient. 15% patients treated with iloperidone discontinued due to TEAEs. Those occurring in ≥1% of patients were: schizophrenia (1.9%), dizziness (1.4%), and QT prolongation (1.1%). One patient died due to alcohol poisoning while receiving iloperidone (0.2%).

In the Relapse Prevention Phase, 40% patients treated with iloperidone vs. (36% patients treated with placebo experienced a TEAE, and 4% patients treated with iloperidone vs. 3% patients treated with placebo experienced a SAE. The most common SAE was schizophrenia: 1.3% in iloperidone-treated patients, 1.3% of placebo-treated patients. No other SAEs occurred in >1 patient.

6% of patients treated with iloperidone vs. 0 patients treated with placebo discontinued due to TEAEs. There were no TEAEs leading to discontinuation that occurred in ≥1 patient. One 47 year-old female patient died due to cardiac arrhythmia of unknown etiology while receiving iloperidone. The day before her death, a routine ECG showed clinically insignificant left ventricular hypertrophy (by voltage only) with normal sinus rhythm and normal QTcF interval (410 msec).

TABLE 6

Incidence of Treatment-Emergent Adverse Events (5% Incidence in any Group, Full Analysis Population)

| | Titration/ Stabilization Phase | Double-Blind Relapse Prevention Phase | | |
|---|---|---|---|---|
| Adverse Event | Total N = 629 n (%) | Iloperidone N = 151 n (%) | Placebo N = 150 n (%) | Total N = 301 n (%) |
| Patients with at least 1 TEAE | 433 (68.8) | 60 (39.7) | 54 (36.0) | 114 (37.9) |
| Schizophrenia | 15 (2.4) | 3 (2.0) | 15 (10.0) | 18 (6.0) |
| Insomnia | 35 (5.6) | 3 (2.0) | 7 (4.7) | 10 (3.3) |
| Dizziness | 73 (11.6) | 4 (2.6) | 4 (2.7) | 8 (2.7) |
| Headache | 40 (6.4) | 3 (2.0) | 5 (3.3) | 8 (2.7) |
| Weight increased | 34 (5.4) | 2 (1.3) | 4 (2.7) | 6 (2.0) |
| Nausea | 32 (5.1) | 2 (1.3) | 0 | 2 (0.7) |
| Somnolence | 52 (8.3) | 2 (1.3) | 0 | 2 (0.7) |
| Dry Mouth | 43 (6.8) | 0 | 0 | 0 |

In the Titration and Stabilization Phase, 4% patients reported akathisia and 3% patients reported extrapyramidal disorder as TEAEs. For global clinical assessment of akathisia using the Barnes Akathisia Scale (BAS), akathisia was absent in 87% of patients at baseline and absent in 97% of patients treated with iloperidone at the end of this phase. No clinically meaningful changes in the Abnormal Involuntary Movement Scale (AIMS) scores were observed.

In the Relapse Prevention Phase, 1% patients treated with iloperidone vs. 0 treated with placebo reported akathisia as a TEAE during the relapse prevention phase. 1% of patients treated with iloperidone vs. 0 treated with placebo reported extrapyramidal disorder as a TEAE during the relapse prevention phase. Akathisia was absent in 95% of iloperidone-treated patients at completion vs. 92% of placebo-treated patients at completion according to the BAS. No clinically meaningful changes in the AIMS scores were observed.

No clinically notable differences in hematology or chemistry parameters expect that 4.5% and 2.6% of patients treated with iloperidone has elevations in BUN and LDL, respectively, vs. none in patients treated with placebo.

In the Titration and Stabilization Phase, the mean change from baseline in weight at the end of the Titration and Stabilization Phase was 0.5 kg in patients treated with iloperidone. 17% of patients treated with iloperidone experienced ≥7% increase in weight from baseline at the end of the Titration and Stabilization Phase.

In the Relapse Prevention Phase, the mean change from baseline in weight at the end of the study was 0.02 kg in patients treated with iloperidone vs. 0.40 kg in patients treated with placebo. 38% of patients treated with iloperidone vs. 31% of patients treated with placebo experienced ≥7% increase in weight from baseline at the end of the study. There were no notable differences in waist circumference at the end of the study.

In the Titration and Stabilization Phase, the mean change from baseline in QTcF for patients treated with iloperidone was 6.4 msec. In the Relapse Prevention Phase, the mean change from baseline in QTcF for patients treated with iloperidone was 4.9 msec vs 1.0 msec in patients treated with placebo.

3. Conclusions

These results showed that flexible dosing of iloperidone was significantly more effective than placebo in the prevention of relapse or impending relapse in patients with schizophrenia who were stabilized on iloperidone treatment, and that long-term treatment with iloperidone is generally safe and well tolerated. The recommended long-term maintenance dose for iloperidone is 6 to 8 mg twice daily (12 to 16 mg/day).

These results further demonstrate a reduction in adverse events in patients administered 16 mg/day or less of iloperidone during such maintenance period. The analysis of safety indicated no new safety signals with respect to long-term use of iloperidone.

As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 24 mg/day, or, more specifically, about 12 mg to about 24 mg," is inclusive of the endpoints and all intermediate values of the ranges of "about 12 mg to about 24 mg," etc.).

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. In a method consisting essentially of treating a schizophrenia patient by administering therapeutic amounts of a compound that is iloperidone or P88 or a pharmaceutically-acceptable salt of iloperidone or P88 daily, the improvement comprising:
   after completion of an acute treatment phase in which the schizophrenia patient is administered the compound at a first dose of 12-24 mg/day, reducing the amount of the compound administered daily to a second dose that is both smaller than the first dose and in a range of 8-16 mg/day.

2. The improvement of claim 1, wherein the first dose is 16-24 mg/day, and the second dose is 12-16 mg/day.

3. The improvement of claim 2, wherein the first dose of 16-24 mg/day is orally administered as 8-12 mg twice daily, and the second dose of 12-16 mg/day is orally administered as 6-8 mg twice daily.

4. The improvement of claim 1, wherein the second dose is about 75% of the first dose.

5. The improvement of claim 2, wherein the first dose is about 16 mg/day and the second dose is about 12 mg/day.

6. The improvement of claim 1, wherein the first dose is about 12 mg/day and the second dose is about 8 mg/day.

7. The improvement of claim 1, wherein the second dose is about 50% of the first dose.

8. The improvement of claim 7, wherein the first dose is about 24 mg/day and the second dose is about 12 mg/day.

9. The improvement of claim 7, wherein the first dose is about 16 mg/day and the second dose is about 8 mg/day.

10. The improvement of claim 1, wherein the second dose is between about 12 mg/day and about 16 mg/day.

11. The improvement of claim 10, wherein the second dose is between about 12 mg/day and about 14 mg/day.

12. The improvement of claim 1, wherein the compound is iloperidone or a pharmaceutically acceptable salt thereof.

13. The improvement of claim 1, wherein the compound is P88 or a pharmaceutically acceptable salt thereof.

* * * * *